(12) United States Patent
Kim et al.

(10) Patent No.: US 9,011,774 B2
(45) Date of Patent: Apr. 21, 2015

(54) DIGITAL BARCODE NANO-WIRE AND SYSTEM FOR BIO-SENSING USING THE SAME

(75) Inventors: CheolGi Kim, Daejeon (KR); Vishnubhotla Sudha Rani, Daejeon (KR); Jong-Ryul Jeong, Daejeon (KR); Seok Soo Yoon, Daegu (KR)

(73) Assignee: The Industry & Academic Cooperation in Chungnam National University, Daejeon (KR)

( * ) Notice: Subject to any disclaimer, the term of this patent is extended or adjusted under 35 U.S.C. 154(b) by 1253 days.

(21) Appl. No.: 12/883,764

(22) Filed: Sep. 16, 2010

(65) Prior Publication Data

US 2011/0236260 A1 Sep. 29, 2011

(30) Foreign Application Priority Data

Mar. 25, 2010 (KR) ........................ 10-2010-0026632

(51) Int. Cl.
| | |
|---|---|
| B82Y 15/00 | (2011.01) |
| B82Y 5/00 | (2011.01) |
| B82Y 25/00 | (2011.01) |
| G01N 33/543 | (2006.01) |

(52) U.S. Cl.
CPC . B82Y 15/00 (2013.01); B82Y 5/00 (2013.01); B82Y 25/00 (2013.01); G01N 33/54326 (2013.01); G01N 33/54373 (2013.01); *Y10S 977/924* (2013.01); *Y10S 977/958* (2013.01)

(58) Field of Classification Search
USPC ............ 422/68.1; 435/287.1, 287.2; 977/924, 977/958
See application file for complete search history.

(56) References Cited

U.S. PATENT DOCUMENTS 7,736,753 B2 * 6/2010 Deligianni et al. ........... 428/678

FOREIGN PATENT DOCUMENTS

KR 20020062283 A 7/2002

OTHER PUBLICATIONS

S. R. Nicewarner-Pena, Submicrometer Metallic Barcodes, 294 Science 137-141 (2001).*
R. L. Stoermer and C. D. Keating, DNA-Directed Assembly of Barcoded Nanowires onto Glass Slides for Biosensing Applications, 5588 Proc. SPIE 51-58 (2004).*
R. L. Stoermer et al., Coupling Molecular Beacons to Barcoded Metal Nanowires for Multiplexed, Sealed Chamber DNA Bioassays, 128 J. Am. Chem. Soc. 16892-16903 (2006).*
J. Wang, Barcoded Metal Nanowires, 18 J. Mater. Chem. 4017-4020 (2008).*
CheolGi, WCU "Next Generation Nanomaterial-based Diagnostic Technique for Bio Medical Application" agency of Chungnam National University, Ceramist, Dec. 31, 2009.

* cited by examiner

*Primary Examiner* — Randy Boyer
(74) *Attorney, Agent, or Firm* — The Webb Law Firm

(57) ABSTRACT

Provided are a barcode nano-wire for decoding a hard magnetic segment by using highly sensitive magnetic sensors and a bio-sensing system using the barcode nano-wire. Integration of hard magnetic and non-magnetic segments produces the barcode nanowire and magnetic segments are detected using highly sensitive magnetoresistance sensors. The non-magnetic segment uses a non-magnetic material and a specific biomolecule for bioanalysis is immobilized at a specific portion of the barcode nano-wire. The hard magnetic material has an advantage of higher coercivity and high remanence magnetization, which is considered as an important parameter in selecting the material. The hard magnetic segments produce distinguishable strong stray fields for individually detecting segments using conventional magnetic sensors for multiplexed bioanalysis.

10 Claims, 4 Drawing Sheets

(a)  (b)  (c)

DIGITAL BARCODE NANO-WIRE AND SYSTEM FOR BIO-SENSING USING THE SAME

CROSS-REFERENCE TO RELATED APPLICATIONS

This application claims priority under 35 U.S.C. §119 to Korean Patent Application No. 10-2010-0026632, filed on Mar. 25, 2010, in the Korean Intellectual Property Office, the disclosure of which is incorporated herein by reference in its entirety.

TECHNICAL FIELD

The following disclosure relates to a digital barcode nano-wire having a multi-segmented hard magnetic/non-magnetic segment structure and a system for bio-sensing using the same, and in particular, to a miniaturized and multiplexed bio analysis device for disease diagnosis and genomics.

BACKGROUND

Recently, miniaturized and multiplexed analysis devices for disease diagnosis as well as genomics generate intense research interest in nano/micro technology-based bio applications. One of the major methods for multiplexing is based on distinguishable particles-based suspension in which each type of probe biomolecules such as protein and deoxyribonucleic acid (DNA) is immobilized.

Many encoding and decoding methods have been developed to attach a unique probe biomolecule to a unique particle in suspension and to detect the target molecule. For example, a diagnostic device using color-coded bead suspension, which contains polystyrene microbeads embedded in red and orange fluorescent dyes at different ratios for yielding distinctive colors, has been already commercialized by the incorporation of flow cytometry technology. The color code is decoded with reflected color image excited by a laser.

Alternatively, a recently developed suspension platform for biosensing uses multi-segmented nanowires, which are fabricated by alternating electrodeposition within a porous template with different metals such as gold (Au), silver (Ag) and copper (Cu) for the respective segments, as "barcodes" for the multiplexing. The barcode is decoded with the difference in optical reflectance of gold and silver segments.

Both of the two representative biosensing technologies, which use suspensions of color-coded microbeads and barcoded nanowires respectively, require laser-based instrumentation, a charge-coupled device (CCD) camera and image processing software for decoding and thus suffer from disadvantages in miniaturization and cost-effectiveness. In addition, the optical detection of nanowires is extremely difficult because nanowire diameters are on the limit of optical detection by a normal microscope. Moreover, it is not so easy to distinguish the barcode segments in these nanowires due to the interference crisis.

On the other hand, magnetic planar tags using an optical-magnetic characteristic in a soft magnetic material have disadvantages because the low remanence magnetization and the information coded on the planar tags may be erased due to small unwanted external magnetic fields. Decoding the information on the planar tags requires optical detection which is expensive to procure.

In order to overcome these disadvantages and to develop sufficiently miniaturized, multiplexed and cost-effective biosensing systems, a novel encoding and decoding method is required.

SUMMARY

An embodiment of the present invention is directed to providing a new type of digital barcode nano-wire for decoding a hard magnetic segment using magnetic sensors.

Another embodiment of the present invention is directed to providing a system for sensing biomolecules by aligning, sorting and decoding a magnetic-based barcode by using magnetic beads or magnetic nanoparticles.

In order to realize the above-mentioned embodiments, provided are a digital barcode nano-wire and a sensing system.

In one general aspect, a digital barcode nano-wire, includes: a hard magnetic segment showing digital information; a non-magnetic segment showing digital information different from the hard magnetic segment; and a spacer that is disposed between the hard magnetic segment and the non-magnetic segment, between the hard magnetic segment and the hard magnetic segment, or between the non-magnetic segment and the non-magnetic segment, and that does not show digital information.

Detecting biomolecules for combining with probe biomolecules formed on a surface of a magnetic bead are formed on the non-magnetic segment surface.

In another general aspect, a digital barcode nano-wire, includes: a hard magnetic segment showing digital information; a non-magnetic segment showing digital information different from the hard magnetic segment; and a spacer that is disposed between the hard magnetic segment and the non-magnetic segment, between the hard magnetic segment and the hard magnetic segment, or between the non-magnetic segment and the non-magnetic segment, and that does not show digital information; and a coating film coating the hard magnetic segment, the spacer and the non-magnetic segment surface with gold (Au) or silver (Ag).

The digital barcode nano-wire has a core-shell structure.

Detecting biomolecules for combining with probe biomolecules formed on a surface of magnetic nano particles are formed on a surface of the coating film.

The hard magnetic segment represents "1" and the non-magnetic segment represents "0".

The hard magnetic segment as a material with large remanence may be formed of any one of hard magnetic materials including CoNiP, CoPtP and CoMnP.

The hard magnetic segment may be formed of gold (Au), silver (Ag) and copper (Cu).

Also, the non-magnetic segment may be formed of gold (Au) or silver (Ag) to immobilize a specific biomolecule for bioanalysis on an end or the entire surface.

In still another general aspect, a bio-sensing system in a fluidic state, includes: a nano-wire inlet introducing a digital barcode nano-wire; a sample inlet introducing a sample; a hybridizing unit forming a hybridized digital barcode nano-wire with the attached sample and a non-hybridized digital barcode nano-wire without the attached sample by hybridizing the digital barcode nano-wire and the sample; an aligning and sorting unit transmitting the hybridized digital barcode nano-wire to a hybridized channel and transmitting the non-hybridized digital barcode nano-wire to a non-hybridized channel by separating the hybridized digital barcode nano-wire and the non-hybridized digital barcode nano-wire; an encoding unit for encoding the separated hybridized digital barcode nano-wire; and a decoding unit decoding the encoded hybridized digital barcode nano-wire.

The encoding unit includes a pulsed magnetic field generator applying pulsed magnetic fields to the hybridized digital barcode nano-wire.

The decoding unit includes a magnetic sensor reading digital information by sensing the encoded hybridized digital barcode nano-wire.

The magnetic sensor may be any one of a semiconductor hall sensor and a magnetoresistance sensor of Giant Magneto Resistance (GMR), Planar Hall Resistance (PHR), and Tunneling Magneto Resistance (TMR).

The magnetic sensor senses the encoded hybridized digital barcode nano-wire at a distance of 10 μm or less from a bottom of the hybridized channel.

The sample is a superparamagnetic bead or a magnetic nano particle and the magnetic nano particle is a constituent element of the magnetic bead and acts as a guiding substance.

The sample is attached to the digital barcode nano-wire through ligand-receptor interaction.

Other features and aspects will be apparent from the following detailed description, the drawings, and the claims.

DETAILED DESCRIPTION OF MAIN ELEMENTS

Figure 1:
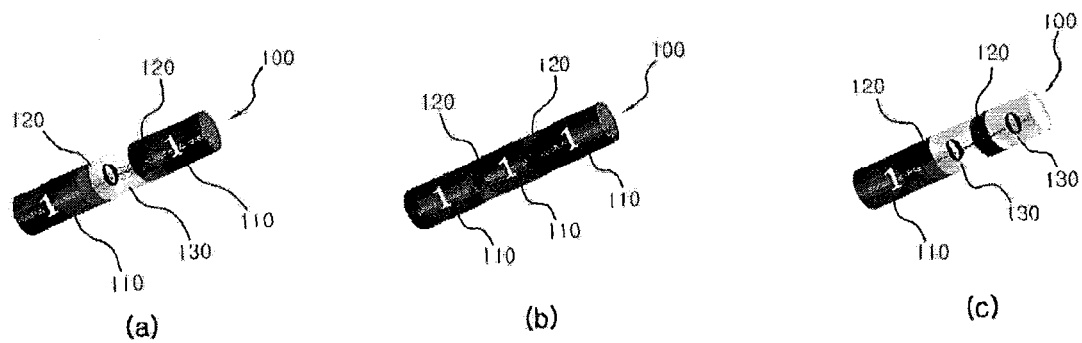
FIG. 1 shows hard magnetic barcode nanowires with three unique digital barcodes according to an exemplary embodiment.

100: barcode nano-wire
100-1: hybridized barcode nano-wire
100-2: barcode nano-wire
101: detecting biomolecules
110: hard magnetic segment
120: spacer
130: non-magnetic segment
200: spherical magnetic bead
200-1: quadrangle magnetic bead
200-2: triangle magnetic bead
210: probe biomolecules
300: coating film
310: magnetic nano particles
311: detecting biomolecules
400: nano-wire inlet
410: sample inlet
420: hybridizing unit
430: aligning and sorting unit
431: upper portion
432: lower portion
440: encoding unit
441: magnetic south pole
442: magnetic north pole
450: decoding unit
451: magnetic sensors
460: hybridized channel
470: non-hybridized channel
490: test-bed

DETAILED DESCRIPTION OF EMBODIMENTS

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, exemplary embodiments will be described in detail with reference to the accompanying drawings.

A digital hard magnetic barcode having following characteristics according to an embodiment of the present invention will be described in easy-to-understand manner.

1. Hard magnetic segments are favored due to high remanence, high coercivity and stronger stray fields; thus these properties are useful for storing encoded information in barcode nanowires using external magnetic fields as well as decoding the magnetic barcode segments using highly sensitive magnetoresistance sensors (magnetic sensor).

2. These barcode nanowires may be used as a platform for multiplexed biosensing when a unique probe biomolecule is attached to a unique digital barcode of the nanowire. Therefore, increasing the number of segments by n increases the multiplexing ability of the barcode nanowires by $2^n$ codes.

3. The development of a multiplexed diagnostic system using barcode nanowires decoding technique is necessary. Accordingly, it is possible to read the hard magnetic barcode segments by the highly sensitive magnetoresistance sensors (magnetic sensor) under incorporation with flow cytometry or magnetic fluidics technologies.

4. This magnetic barcode is encoded by a magnetic field and decoded by a magnetic sensor. Accordingly, the magnetic barcode system is more compact and cost-effective than general biosensing systems used for optical encoding and decoding methods.

The digital hard magnetic barcode according to an embodiment of the present invention will be described in detail with reference to the accompanying drawings hereinafter.

FIG. 1 shows hard magnetic barcode nanowires with three unique digital barcodes according to an exemplary embodiment. That is, FIGS. 1(a), 1(b) and 1(c) show the hard magnetic barcode nanowires 100 with digital barcodes 101, 111 and 100. The hard magnetic barcode nanowires 100 are the combination of a hard magnetic segment and a non-magnetic segment.

The hard magnetic barcode nanowires 100 adopt a multi-segmented nano-wire suspension method and the multi-segmented nano-wire suspension is fabricated by alternating electrodeposition with non-magnetic segment materials and hard magnetic materials.

These barcodes are synthesized with different units and represent a non-magnetic segment as "0", a hard magnetic segment as "1", a non-magnetic segment as "1", and a hard magnetic segment as "0".

As shown in FIG. 1, the hard magnetic barcode nanowires 100 include three segments and a spacer 120 is disposed between the segments.

For example, '0' represents a non-magnetic segment 130 and '1' represents a remanence material segment 110. Also, the spacer 120 as a conductor represents a portion, which does not include information. The remanence materials include CoNiP, CoPtP, CoMnP and SmCoP. The non-magnetic segments include gold (Au), silver (Ag) and copper (Cu). The spacer includes non-magnetic gold (Au), silver (Ag), and copper (Cu).

In FIG. 1(*a*), a barcode is marked as '101', which includes the remanence material segment 110, the spacer 120, the non-magnetic segment 130, the spacer 120, and the remanence material segment 110 in order from the left side. In FIG. 1(*b*), a barcode is marked as '111'. In FIG. 1 (*c*), a barcode is marked as '100'.

That is, the barcode '111' includes only the remanence material segment 110. The spacer 120 is included between the remanence material segment 110 and the remanence material segment 110. In FIG. 1(*c*), the barcode '100' includes the remanence material segment 110, the spacer 120, the non-magnetic segment 130, the spacer 120, and the non-magnetic segment 130 in order from the left side.

Biomolecules such as protein and deoxyribonucleic acid (DNA) may be easily separated and detected by using the hard magnetic barcode nanowires 100. The hard magnetic segment 110 may be used for decoding by highly sensitive magnetic sensors and the spacer 120 is used for immobilizing a specific biomolecule.

In the exemplary embodiment of the present invention, the hard magnetic barcode nanowires 100 are illustrated as a circular shape but are not limited thereto. Shapes such as quadrangle, hexagon and octagon may be used.

Figure 2:
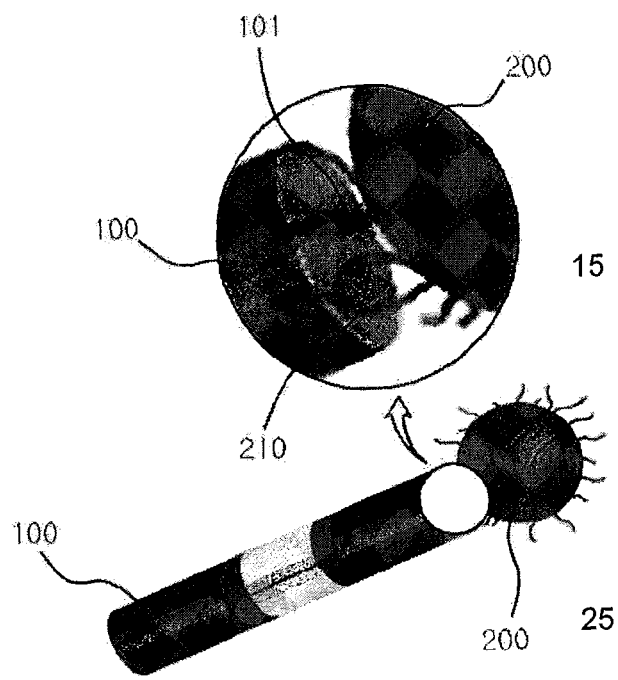
FIG. 2 shows nanowires attached to the superparamagnetic magnetic beads functionalized through specific ligand-receptor interaction according to an exemplary embodiment.

A method for attaching a magnetic bead to the hard magnetic barcode nanowires 100 shown in FIG. 1 will be described hereinafter and is shown in FIG. 2. FIG. 2 shows the nanowires attached to superparamagnetic magnetic beads functionalized through specific ligand-receptor interaction according to an exemplary embodiment.

With reference to FIG. 2, the spherical magnetic bead 200 is attached to one end of the hard magnetic barcode nanowires 100. Probe biomolecules 210 are randomly attached on the surface of the spherical magnetic bead 200 and detecting biomolecules 101 are also randomly attached on the surface of the hard magnetic barcode nanowires 100.

The spherical magnetic bead 200 is formed by coating magnetic nano particles, e.g., metals and oxides, with substances such as polystyrene having excellent insulating properties and transparency. Each of the detecting biomolecules 101 and the probe biomolecules 210 is formed on the surface by immersing the hard magnetic barcode nanowires 100 and the spherical magnetic bead 200 in a specific solution of different biomolecules.

Therefore, the detecting biomolecules 101 formed on the surface of the non-magnetic barcode nanowires 100 and the probe biomolecules 210 formed on the surface of the spherical magnetic bead 200 are attached through ligand-receptor interaction. It is shown in an expanded figure. That is, the probe biomolecules 210 and the detecting biomolecules 101 are connected only when they have the same property that interaction is possible.

The spherical magnetic bead 200 may be a superparamagnetic bead. The superparamagnetic bead 200 acts as a guiding object of the functionalized barcode nanowires 100 for aligning and sorting in a microfluidic channel. The hard magnetic barcode nanowires 100 do not have remanence until magnetic fields are applied.

Figure 3:
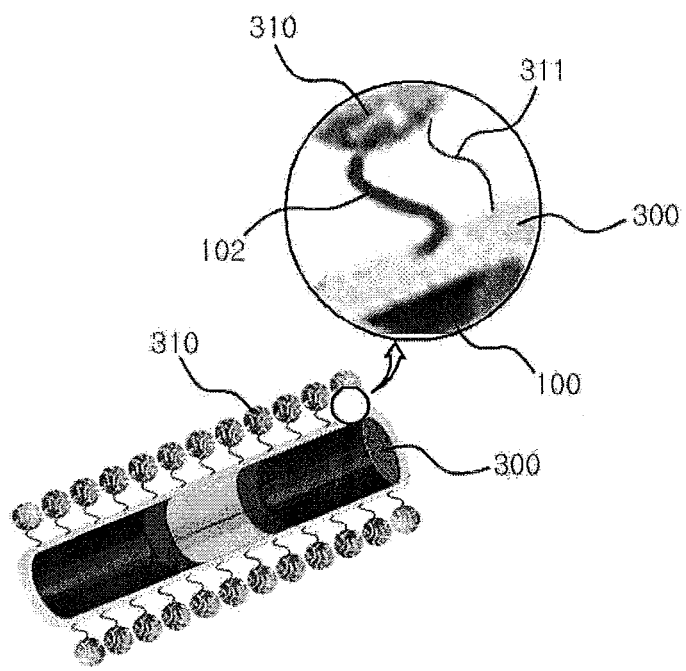
FIG. 3 shows a core-shell structure of the barcode nanowires according to an exemplary embodiment.

FIG. 3 shows a core-shell structure of the barcode nanowires according to an exemplary embodiment. With reference to FIG. 3, the coating film 300 with gold (Au) or copper (Cu) coating is formed on the surface of the hard magnetic barcode nanowires 100.

Therefore, the hard magnetic barcode nanowires 100 have a shape of a core-shell type. Magnetic nano particles 310 are attached on the surface of the coating film 300 through the probe biomolecules 311 and detecting biomolecules 102. Since the description on the probe biomolecules 311 and the detecting biomolecules 102 is similar to that in FIG. 2, it will not be provided herein.

The magnetic nano particles 310 are particles included inside the spherical magnetic bead 200 shown in FIG. 2 and metal materials or oxides are used. The magnetic nano particles 310 is attached on the surface of the coating film 300 through hybridization of a specific biomolecule. Aligning and sorting of the hard magnetic barcode nanowires 100 of the core-shell type are performed in the microfluidic channel by applying external magnetic fields on a microfluidic wall.

That is, only the hybridized barcode nanowires 100 may be aligned and sorted as a specified channel by applying the magnetic fields inside the fluidic channel. The non-hybridized barcode nanowires 100 may be aligned and sorted as other channels different from the specified channel.

With reference to FIGS. 1 to 3, a procedure of encoding, decoding aligning and sorting the hard magnetic barcode nanowires 100 inside the fluidic channel will be described. It will be conceptually shown in FIG. 4.

Figure 4:
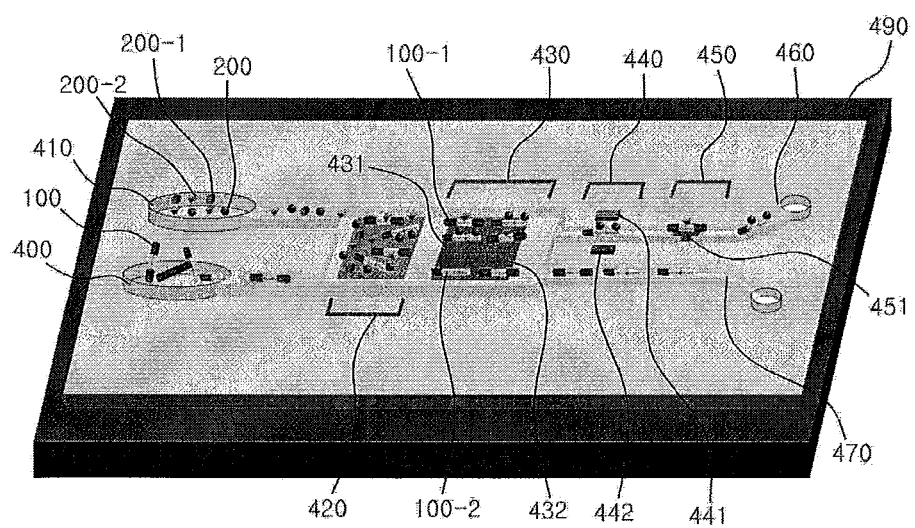
FIG. 4 is a system showing a method for aligning and sorting along with encoding and decoding concept of barcode nanowires inside a fluidic channel according to an exemplary embodiment.

FIG. 4 is a system showing a method for aligning and sorting along with encoding and decoding concept of barcode nanowires inside the fluidic channel according to an exemplary embodiment. With reference to FIG. 4, a test-bed 490 for encoding, decoding and aligning and sorting the hard magnetic barcode nanowires 100 illustrated in FIGS. 1 to 3 is disposed.

A sample inlet 410 for introducing the magnetic bead 200 as a bio analyte, a nano-wire inlet 400 for introducing the hard magnetic barcode nanowires 100, a hybridizing unit 420 for hybridizing the magnetic bead 200 and the hard magnetic barcode nanowires 100, an aligning and sorting unit 432 for separating a hybridized barcode nano-wire from a non-hybridized barcode nano-wire, an encoding unit 440 for performing encoding by applying magnetic fields to the hybridized barcode nanowires 100-1, and a decoding unit 450 for decoding the encoded hybridized barcode nanowires 100-1 are included on the test-bed 490. Herein, the hybridized state means a state that the magnetic bead 200 is attached to the barcode nanowires 100 and the non-hybridized state means a state that the magnetic bead 200 is not attached to the barcode nanowires 100.

A procedure of encoding, decoding, aligning and sorting performed on the test-bed 490 will be described as follows.

Each of magnetic beads 200, 200-1 and 200-2 and the hard magnetic barcode nanowires 100 is introduced through the sample inlet 410 and the nano-wire inlet 400. The magnetic beads have different shapes according to the type of biomolecules. FIG. 4 shows the spherical magnetic bead 200, the quadrangle magnetic bead 200-1, and the triangle magnetic bead 200-2. The shape of the magnetic beads is not limited and shapes such as a hexagon shape are also possible. Also, other colors will be possible.

The introduced magnetic beads 200, 200-1 and 200-2 and the hard magnetic barcode nanowires 100 are hybridized in the hybridizing unit 420. That is, as shown in FIG. 2 or 3, the magnetic beads 200, 200-1 and 200-2 are attached on the surface of the non-magnetic barcode segments 100. The surfaces of the probe biomolecules 210 (see FIG. 2) of the magnetic beads 200, 200-1 and 200-2 and detecting biomolecules 101 (see FIG. 2) on the non-magnetic barcode segments 100 are combined by ligand-receptor interaction. At this time, there is no remanence magnetization of the hard magnetic barcode nanowires 100.

The barcode nanowires 100, to which the magnetic beads 200, 200-1 and 200-2 are attached inside the hybridizing unit 420, become the hybridized barcode nanowires 100-1. The barcode nanowires 100, to which the magnetic beads 200, 200-1 and 200-2 are not attached, become the non-hybridized barcode nanowires 100-2.

In order to separate the hybridized barcode nanowires 100-1 and the non-hybridized barcode nanowires 100-2, the aligning and sorting procedure by the aligning and sorting unit 430 is followed. That is, when the hybridized barcode nanowires 100-1 and the non-hybridized barcode nanowires 100-2 enter inside the aligning and sorting unit 430, the hybridized barcode nanowires 100-1 is located in an upper portion 431 inside the aligning and sorting unit 430 and the non-hybridized barcode nanowires 100-2 is located in a lower portion 432 inside the aligning and sorting unit 430.

The barcode nanowires 100-1 and 100-2 separated in the aligning and sorting unit 430 progress along a hybridized channel 460 and a non-hybridized channel 470. That is, the hybridized barcode nanowires 100-1 progress toward the hybridized channel 460 and the non-hybridized barcode nanowires 100-2 progress toward the non-hybridized channel 470. That is, aligning and sorting of the barcode nanowires 100-1 and 100-2 are performed in the test-bed 490 according to two different methods.

In a first case, the hybridized barcode nanowires 100-1, to which the magnetic beads 200, 200-1 and 200-2 are attached, are aligned and sorted by using lithographically patterned magnetic pathways within the test-bed 490. That is, when the pathways inside the test-bed 490 are affected by external oscillating magnetic fields, the hybridized barcode nanowires 100-1 are aligned and sorted toward the upper portion 431 by the magnetic beads 200, 200-1 and 200-2 as a barcode guiding object through the magnetic pathways. When the microfluidic channels 460 and 470 are under oscillating magnetic fields, the magnetic beads 200, 200-1 and 200-2 attached to the hybridized barcode nanowires 100-1 acts as a guiding object of the functionalized barcode nanowires 100-1. That is, the hybridized barcode nanowires 100-1 are aligned and sorted toward the hybridized channel 460.

In a second case, the hard magnetic barcode nanowires 100 having the non-magnetic segment 130 of FIG. 1 are aligned and sorted in the lower portion 432 of the aligning and sorting unit 430 by application of a small magnetic field gradient. That is, the non-hybridized barcode nanowires 100-2 are aligned and sorted toward the non-hybridized channel 470.

The hybridized barcode nanowires 100-1 progressed toward the hybridized channel 460 are encoded in the encoding unit 440. In other words, encoding of the non-magnetic segment 130 and the hard magnetic segment 110 of FIG. 1 included in the hybridized barcode nanowires 100-1 is performed by using pulsed magnetic fields generated by magnetisms 441 and 442, i.e., a magnetic north pole 441 and a magnetic south pole 442 included in up and down parts. Accordingly, the hybridized barcode nanowires 100-1 create remanence.

When the hybridized barcode nanowires 100-1, to which the magnetic beads 200, 200-1 and 200-2 are attached, enter the decoding unit 450, a decoding procedure is performed. That is, the segments 110 and 130 included in the hybridized barcode nanowires 100-1 are decoded.

The decoding is performed through highly sensitive magnetic sensors 451. Semiconductor hall sensors and magnetoresistance sensors such as Giant Magneto Resistance (GMR), Planar Hall Resistance (PHR) and Tunneling Magneto Resistance (TMR) may be used as these magnetic sensors.

That is, the hybridized barcode nanowires 100-1 are encoded into high magnetic fields by the magnetism 441 and 442 of the encoding unit 440 and decoded by the highly sensitive magnetic sensors 451. Therefore, the encoded information is read as digital information, i.e., the barcodes 101, 111 and 100. Although it is not shown in the drawings, singularities of the biomolecule as a sample may be analyzed by connecting a computer (not shown) to the magnetic sensors 451. The non-hybridized barcode nanowires 100-2 is separated by applying micro magnetic fields to the non-hybridized channel 470.

Based on the above-mentioned barcode nano-wire, it is possible to align and sort the hybridized nano-wire with a proper bioagent and then recognize the singularity of the bioagent.

Figure 5:
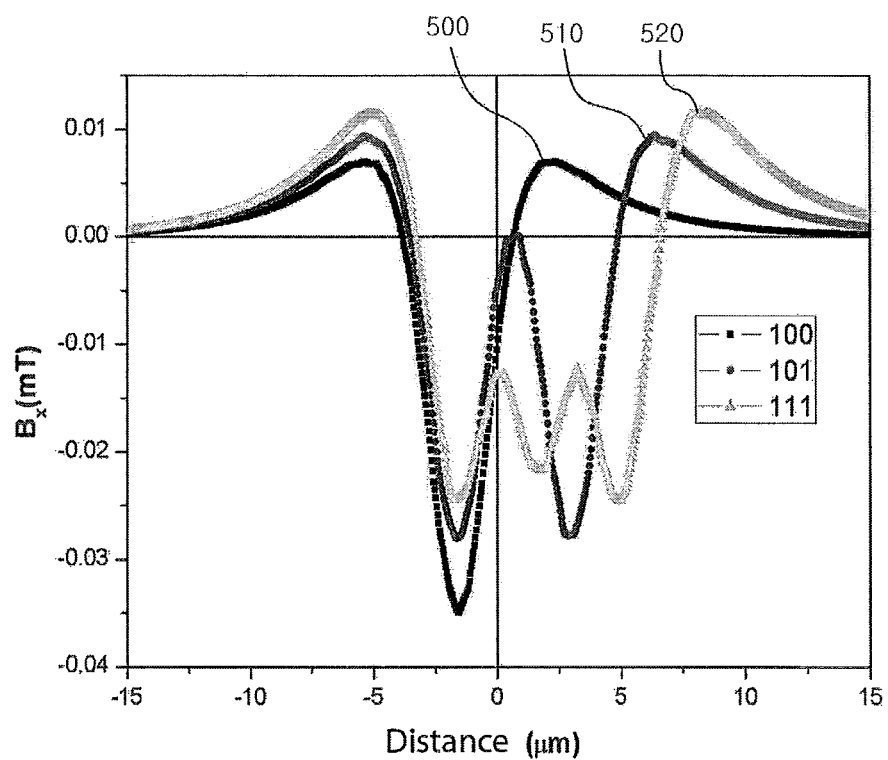
FIG. 5 is a graph showing a sensor signal variation with respect to different codes of the barcode nanowires according to an exemplary embodiment.

FIG. 5 is a graph showing a sensor signal variation with respect to different codes of the barcode nanowires according to an exemplary embodiment. FIG. 5 shows a calculated magnetic field $B_x$ in a wire direction for the different codes of the barcode nanowires such as digital information 100, 101 and 111. That is, lines 500, 510 and 520 respectively represent the digital information 100, 101 and 111.

It is considered that the calculated magnetic field $B_x$ keeps a constant distance of 3 μm from the nanowires of three different barcodes 100, 101 and 111, i.e., a distance between the surface of the magnetic sensor 451 in FIG. 4 and the hard magnetic barcode nanowires 100. Accordingly, it is possible to observe the magnetic field distribution of the individual barcode hard magnetic segment 110 separated by the non-magnetic segment 130 of FIG. 1.

Figure 6:
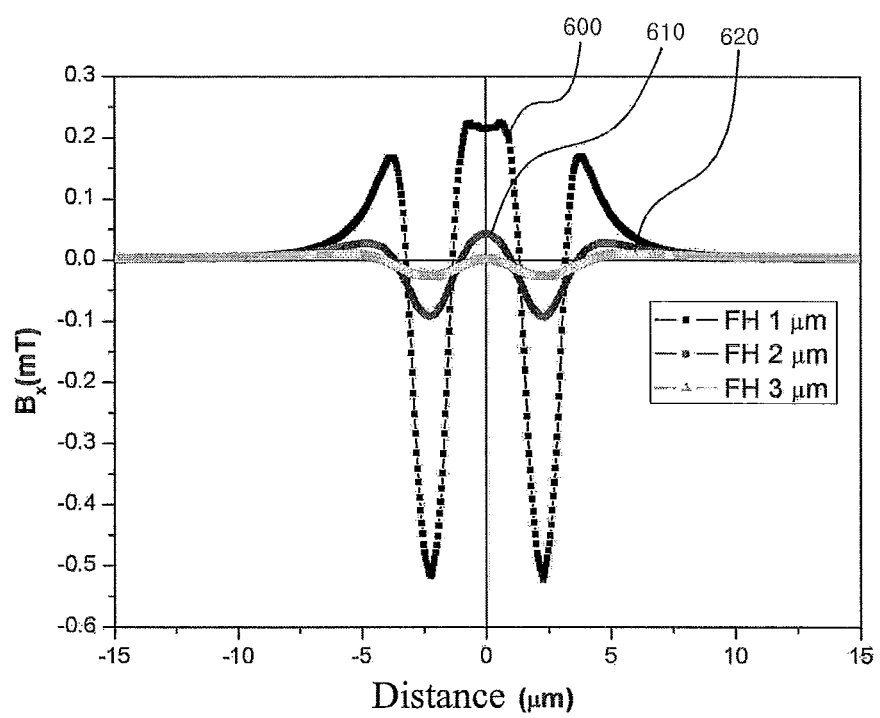
FIG. 6 is a graph showing a sensor signal variation depending on both a distance of the sensor from the nanowires and code information according to an exemplary embodiment.OF MAIN ELEMEMTS

FIG. 6 is a graph showing a sensor signal variation depending on both a distance of the sensor from the nanowires and code information according to an exemplary embodiment. FIG. 6 shows the calculated magnetic fields $B_x$ in the wire direction depending on both flying heights of the barcode nano-wires and barcodes 100, 101 and 111. The flying height means the height of the hard magnetic barcode nanowires 100 from the floor of the microfluidic channels 460 and 470.

In FIG. 6, when the flying height is 1 μm, a calculated value $B_x$ for CoNiP is 0.5 mT. Based on the $B_x$ magnetic fields calculation, the detectable range is several μm with respect to the CoNiP barcode nanowires using the magnetic sensors 451. Preferably, the detectable range is from 0.5 μm to 10 μm but is not limited thereto.

In case of Planar Hall Resistance (PHR) sensor as one of the magnetic sensors, magnetic sensitivity, i.e., output voltage change according to the variation of the magnetic field, is 60 μV/mT and detection limit is 0.001 mT in general.

According to the present invention, since encoding and decoding are performed by using the barcode nano-wire formed of the multiplexed segments, it is possible to build an effective bio-sensing system.

In addition, the present invention aligns and sorts the barcode nano-wire by using the magnetic bead or magnetic nanoparticles in the barcode nano-wire. Accordingly, the magnetic barcode system is more compact and cost-effective than the general biosensing systems to make multiple-detecting possible.

Although preferred embodiments of the present invention are described with reference to accompanying drawings, it will be apparent by a person having an ordinary skill in the art that the scope of the present invention is not limited thereto and diverse modifications are also possible. Therefore, the scope of the present invention should be determined by the accompanying claims and their equivalents.

What is claimed is:

1. A bio-sensing system in a fluidic state, comprising:
   a nano-wire inlet introducing a digital barcode nano-wire;
   a sample inlet introducing a sample;
   a hybridizing unit configured to form a hybridized digital barcode nano-wire with the attached sample and a non-hybridized digital barcode nano-wire without the attached sample by hybridizing the digital barcode nano-wire and the sample; an aligning and sorting unit configured to transmit the hybridized digital barcode nano-wire to a hybridized channel and transmitting the non-hybridized digital barcode nano-wire to a non-hybridized channel by separating the hybridized digital barcode nano-wire and the non-hybridized digital barcode nano-wire;
   an encoding means for encoding the separated hybridized digital barcode nano-wire; and
   a decoding means decoding the encoded hybridized digital barcode nano-wire.

2. The bio-sensing system of claim 1, wherein the encoding means includes a pulsed magnetic field generator applying pulsed magnetic fields to the hybridized digital barcode nano-wire, and
   the decoding means includes a magnetic sensor reading digital information by sensing the encoded hybridized digital barcode nano-wire.

3. The bio-sensing system of claim 2, wherein the magnetic sensor is any one of a semiconductor hall sensor and a magnetoresistance sensor of Giant Magneto Resistance (GMR), Planar Hall Resistance (PHR), and Tunneling Magneto Resistance (TMR).

4. The bio-sensing system of claim 2, wherein the magnetic sensor senses the encoded hybridized digital barcode nano-wire at a distance of 10 μm or less from a bottom of the hybridized channel.

5. The bio-sensing system of claim 1, wherein the sample is a superparamagnetic bead or a magnetic nano particle and the magnetic nano particle is a constituent element of the magnetic bead and acts as a guiding substance.

6. The bio-sensing system of claim 1, wherein the sample is attached to the digital barcode nano-wire through ligand-receptor interaction.

7. The bio-sensing system of claim 1, wherein said digital barcode nano-wire comprises:
   a hard magnetic segment showing digital information;
   a non-magnetic segment showing digital information different from the hard magnetic segment; and
   a spacer that is disposed between the hard magnetic segment and the non-magnetic segment, between the hard magnetic segment and the hard magnetic segment, or between the non-magnetic segment and the non-magnetic segment, and that does not show digital information; and
   a coating film coating the hard magnetic segment, the spacer and the non-magnetic segment surface with gold (Au) or silver (Ag),
   wherein detecting biomolecules for combining with probe biomolecules formed on a surface of magnetic nano particles are formed on a surface of the coating film.

8. The bio-sensing system of claim 7, wherein the hard magnetic segment represents "1" and the non-magnetic segment represents "0".

9. The bio-sensing system of claim 7, wherein the hard magnetic segment represents "0" and the non-magnetic segment represents "1".

10. The bio-sensing system of claim 7, wherein the hard magnetic segment as a remanence material is formed of any one of CoNiP, CoPtP and CoMnP; the non-magnetic segment is formed of gold (Au) or silver (Ag) to immobilize a specific biomolecule for bioanalysis; and the spacer is formed of copper (Cu).

* * * * *